United States Patent [19]

Degner et al.

[11] Patent Number: 4,814,510

[45] Date of Patent: Mar. 21, 1989

[54] NOVEL BENZALDEHYDE DERIVATIVES, THEIR PREPARATION, AND THEIR USE

[75] Inventors: Dieter Degner, Dannstadt-Schauernheim; Walter Gramlich, Edingen-Neckarhausen; Heinz Hannebaum, Ludwigshafen, all of Fed. Rep. of Germany

[73] Assignee: BASF Aktiengesellschaft, Ludwigshafen, Fed. Rep. of Germany

[21] Appl. No.: 132,130

[22] Filed: Dec. 14, 1987

[30] Foreign Application Priority Data

Dec. 23, 1986 [DE] Fed. Rep. of Germany ....... 3644076

[51] Int. Cl.$^4$ ..................... C07C 43/30; C07C 45/00; C07C 47/198
[52] U.S. Cl. ................. 568/425; 568/426; 568/469.9; 568/485; 568/592
[58] Field of Search ................ 568/425, 426, 469.9, 568/485, 592

[56] References Cited

U.S. PATENT DOCUMENTS

| 4,148,696 | 4/1979 | Halter | 568/425 |
| 4,152,230 | 5/1979 | Edwards et al. | 568/425 |
| 4,582,942 | 4/1986 | Comninellis et al. | 568/425 |

FOREIGN PATENT DOCUMENTS

| 2201837 | 9/1987 | Japan | 568/426 |
| 0793986 | 1/1981 | U.S.S.R. | 568/425 |

*Primary Examiner*—Werren B. Lone
*Attorney, Agent, or Firm*—John H. Shurtleff

[57] ABSTRACT

Benzaldehyde derivatives of the general formula I, where X is an oxygen atom or two $R^2O$ groups and $R^1$ and $R^2$ are alkyl radicals of 1-4 carbon atoms, their preparation, and their use as odorants or odorant intermediates.

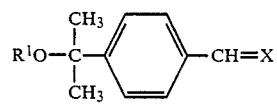

I

11 Claims, No Drawings

NOVEL BENZALDEHYDE DERIVATIVES, THEIR PREPARATION, AND THEIR USE

The present invention relates to novel benzaldehyde derivatives, their preparation, and their use as odorants or odorant intermediates.

It is known that benzaldehydes substituted in the 4-position are used as odorants. For instance, 4-methylbenzaldehyde (p-tolualdehyde) has a bitter-sweet, bitter-almond-like odor; 4-methoxybenzaldehyde (anisaldehyde) in contrast has an intense, sweet-flowery, somewhat hay-like odor; 4-isopropylbenzaldehyde (cumaldehyde) has a strong, almost unpleasant, green-bitter odor.

We have found that the novel 4-alkoxyalkyl-substituted benzaldehyde derivatives of the general formula I—where X is an oxygen atom or two $R^2O$ groups and $R^1$ and $R^2$ are alkyl radicals of 1–4 carbon atoms—are valuable odorants or odorant intermediates.

The novel benzaldehyde derivatives are either 4-(1-alkoxy-1-methylethyl)benzaldehydes of the formula (II) or 4-(1-alkoxy-1-methylethyl)-benzaldehyde dialkyl acetals of the formula (III), where $R^1$ and $R^2$ are alkyl radicals of 1–4 carbon atoms.

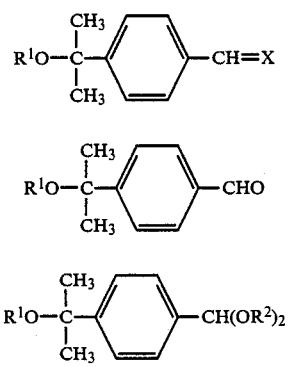

The aldehydes II have, for instance, an odor having a very fine dry, sweetish woody note, which clearly differs from the bitter note of previously known benzaldehydes substituted in the 4-position.

In the formulae I to III the alkyl radicals are methyl, ethyl, propyl, or isopropyl, for example. The following novel benzaldehyde derivatives are named as examples: 4-(1-methoxy-1-methylethyl)benzaldehyde dimethyl acetal, 4-(1-methoxy-1-methylethyl)benzaldehyde, 4-(1-ethoxy-1-methylethyl)benzaldehyde diethyl acetal, 4-(1-ethoxy-1-methylethyl)benzaldehyde.

The novel acetals III can be prepared by a particularly elegant method of performing the invention whereby benzene derivatives of the general formula IV are oxidized electrochemically in the presence of an alkanol ROH; X is a hydrogen atom or an alkoxy $R^1O$, Z is methyl, alkoxymethyl $R^2OCH_2$—, or dialkoxymethyl $(R^2O)_2CH$— (in the last case X must be hydrogen), and R, $R^1$, and $R^2$ are alkyls of 1–4 carbon atoms.

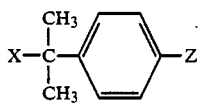

Examples of intermediates for the preparation of the novel acetals III are 4-isopropyltoluene, 4-(1-methoxy-1-methylethyl)toluene, 4-(1-ethoxy-1-methylethyl)toluene, 4-isopropylbenzaldehyde dimethyl acetal, and 4-isopropylbenzaldehyde diethyl acetal. Methanol and ethanol are the alkanols of choice.

The novel process does not necessitate a special cell design; it is preferably carried out in an undivided flow cell. Noble-metal electrodes such as platinum or oxide electrodes such as titanium/ruthenium dioxide are suitable as anodes, but the preferred material is graphite. For the cathodes materials such a steel, iron, nickel, cooper, zinc, or carbon can be considered, but graphite is preferred. The electrolyte consists of the alkanol ROH, the compound of general formula IV, and a conductive sald. The conductive salt can be a neutral salt, but also an acid or base. Examples of neutral salts are fluorides such a potassium fluoride, sulfonates such as sodium benzenesulfonate, sulfates such as tetramethylammonium methylsulfate, tetrafluoroborates such as sodium tetrafluoroborate, phosphates, and phosphonates. Examples of acids are sulfuric acid, alkanesulfonic acids, and arenesulfonic acids; alkoxides such as sodium methoxide and hydroxides such as potassium hydroxide are examples of suitable bases. The electrolyte can, for instance, have the following composition in parts by weight:

Compound of formula IV 3–60%
Alkanol ROH 35–90%
Conductive salt 0.5–10%

In the novel process the current density can be chosen from a wide range of values, e.g. 0.5–20 $A/dm^2$, but values of 1–8 $A/dm^2$ are preferred. During the electrolysis the temperature can be, for instance, 20°–60° C. Preferably the electrolysis is carried out under atmospheric pressure. The intermediates of general formula IV can be converted to a great extent; unconverted compound and products remaining from intermediate stages can be returned to the electrolyte. The electrolysis can be carried out batchwise or continuously.

The electrolysis product is subsequently treated by conventional methods. If it is acid it is first neutralized with a base such as sodium methoxide. Excess alkanol is distilled off. The conductive salt is filtered off and can be returned to the electrolysis, together with the alkanol, if need be. The crude acetal can be further purified, e.g. by rectification.

The novel benzaldehydes II can be prepared very advantageously by hydrolysis of the acetals III in a conventional manner, e.g. by heating them with water under reflux.

The hydrolysis can be conducted batchwise or continuously. The alkanol ROH that is formed can conveniently be used again for the preparation of acetals III. The novel benzaldehydes can be separated by phase separation if excess water is used for the hydrolysis. If required the novel benzaldehydes can be further purified by distillation.

The benzaldehydes II are used as odorants or constituents of perfumery oils, on account of the properties mentioned above. They adhere extraordinarily, and can be combined very well with the usual perfume constituents and other odorants, giving novel compositions, to which they impart very good adherence also. The proportion of the novel benzaldehydes in these compositions is generally 1–50% by weight. The compositions can be employed in extract perfumery and for perfuming cosmetic preparations such as skin creams, lotions, toilet waters, aerosols, soaps, mouthwashes, etc. They can also be used as reodorants for industrial products such as washing powders, cleaning liquids, and softening rinses.

EXAMPLE 1

Electrosynthesis of 4-(1-methoxy-1-methylethyl)benzaldehyde dimethyl acetal from 4-(1-methoxy-1-methylethyl)toluene.

Apparatus: undivided cell with five electrodes, electrode spacing 1.5 mm; graphite anodes and cathodes.

The first charge of electrolyte is made up with the following composition: 4-(1-methoxy-1-methylethyl)toluene (14.03 kg), potassium benzenesulfonate (0.63 kg), benzenesulfonic acid (0.16 kg), methanol (62.2 kg).

The electrolysis is carried out at a temperature of 26° C. with 11 F/mol—based on 4-(1-methoxy-1-methylethyl)toluene—and a current density of 3.6 A/dm$^2$. The electrolyte is pumped into the cell via a heat exchanger at 800 l/h.

A second charge of electrolyte with the following composition is electrolyzed in the same way as the first: 4-(1-methoxy-1-methylethyl)toluene (11.83 kg), potassium benzenesulfonate (0.68 kg), benzenesulfonic acid (0.17 kg), methanol (67.7 kg).

The products of both electrolyses are combined and subjected to subsequent treatment.

The methanol is first distilled off at atmospheric pressure until the temperature of the still bottoms reaches 125° C. The residue is cooled to about 30° C. and filtered through a pressure nutsche, giving 0.9 kg of a salt that can be returned for electrolysis, together with the methanol. The filtrate (43.3 kg) is then rectified with a head pressure of 2 mbar and head temperatures of 100°–120° C. The following are obtained: 4-(1-methoxy-1-methylethyl)toluene (0.17 kg), 1-methoxymethyl-4-(1-methoxy-1-methylethyl)benzene (1.54 kg), and 4-(1-methoxy-1-methylethyl)benzaldehyde dimethyl acetal (20.88 kg)—b.p. 108° C./3 mbar; HNMR: (CH$_3$)$_2$C— 1.53 p.p.m. (s), =CO(CH$_3$)— 3.05 p.p.m. (s), =C(OCH$_3$)$_2$ 3.35 p.p.m. (s), Ar-CH(O-)$_2$ 5.38 p.p.m. (s), ArH 7.44 p.p.m. (s).

The conversion of 4-(1-methoxy-1-methylethyl)toluene is calculated as 99.3%, the yield of 1-methoxymethyl-4-(1-methoxy-1-methylethyl)benzene is 5%, and the yield of 4-(1-methoxy-1-methylethyl)benzaldehyde dimethyl acetal is 59.1%. The selectivity for the dimethyl acetal is 62.7%. The unchanged starting compound and the 1-methoxymethyl-4-(1-methoxy-1-methylethyl)benzene can be returned for electrolysis.

EXAMPLE 2

Electrosynthesis of 4-(1-methoxy-1-methylethyl)benzaldehyde dimethyl acetal from 4-isopropyltoluene Apparatus: undivided cell with eleven electrodes, electrode spacing 0.5 mm; graphite anodes and cathodes.

The electrolysis is carried out with electrolyte of the following composition: 4-isopropyltoluene (285 g), sodium benzenesulfonate (30 g), methanol (2670 g). The electrolysis is carried out at a temperature of 35°–42° C. with 13.5 F/mol—referred to the 4-isopropyltoluene—and a current density of 1.7 A/dm$^2$. The electrolyte is pumped into the cell via a heat exchanger at 200 l/h.

Subsequent treatment is similar to that in Example 1, and yields 154.2 g of 4-(1-methoxy-1-methylethyl)benzaldehyde dimethyl acetal. The following compounds, which can be returned for electrolysis, are also obtained: 4-isopropyltoluene (5.9 g), 4-(1-methoxy-1-methylethyl)toluene (0.9 g), 1-isopropyl-4-methoxymethylbenzene (1.7 g), 4-isopropylbenzaldehyde dimethyl acetal (50.2 g), and 1-methoxymethyl-4-(1-methoxy-1-methylethyl)benzene (3.1 g).

The calculated yield of 4-(1-methoxy-1-methylethyl)benzaldehyde dimethyl acetal is 32.4%, and the selectivity for this acetal is 38.1%.

EXAMPLE 3

Electrosynthesis of 4-(1-methoxy-1-methylethyl)benzaldehyde dimethyl acetal from 4-isopropylbenzaldehyde dimethyl acetal.

Apparatus: undivided cell with eleven elctrodes, electrode spacing 1 mm; graphite anodes and cathodes.

The electrolysis is carried out with electrolyte of the following composition: 4-isopropylbenzaldehyde dimethyl acetal (300 g), potassium benzenesulfonate (30 g), methanol (2670 g). The electrolysis is carried out at a temperature of 26°–29° C. with 12 F/mol—based on 4-isopropylbenzaldehyde dimethyl acetal—and a current density of 3.3 A/dm$^2$. The electrolyte is pumped into the cell via a heat exchanger at 200 l/h.

Subsequent treatment is similar to that in Example 1, and yields unconverted 4-isopropylbenzaldehyde dimethyl acetal (25 g) and 4-(1-methoxy-1-methylethyl)benzaldehyde dimethyl acetal (72 g).

The conversion of 4-isopropylbenzaldehyde dimethyl acetal is 92%; the yield of 4-(1-methoxy-1-methylethyl)benzaldehyde dimethyl acetal is 21%, and the selectivity for the latter is 23%.

EXAMPLE 4

Electrosynthesis of 4-(1-ethoxy-1-methylethyl)benzaldehyde diethyl acetal from 4-(1-ethoxy-1-methylethyl)toluene.

Apparatus: undivided cell with nine electrodes, electrode spacing 0.5 mm; graphite anodes and cathodes.

The electrolysis is carried out with electrolyte of the following composition: 4-(1-ethoxy-1-methylethyl)toluene (390 g), benzenesulfonic acid (21.7 g), sodium benzene sulfonate (21.7 g), ethanol (3666 g).

The electrolysis is carried out at a temperature of 60° C. with 8.3 F/mol—based on 4-(1-ethoxy-1-methylethyl)toluene—and a current density of 1.3 A/dm$^2$. The electrolyte is pumped into the cell via a heat-exchanger at 300 l/h.

In the subsequent treatment the electrolyte is first neutralized with sodium ethoxide. Ethanol is distilled off at atmospheric pressure until the temperature of the bottoms reaches 120° C. The conductive salt (58 g) is filtered off, and the filtrate is fractionated with a head pressure of 6 mbar and head temperatures of 85°–135° C. This yields 151.4 g of 4-(1-ethoxy-1-methylethyl)benzaldehyde diethyl acetal. HNMR: 1.15–1.35 ppm (m), 1.55 ppm (s), 3.25 ppm (q), 3.5–3.7 ppm (m), 5.5 ppm (s), 7.45 ppm (s).

The following compounds, which can be returned for electrolysis, are also obtained: 4-(1-ethoxy-1-methylethyl)toluene (5.7 g) and 1-ethoxymethyl-4-(1-ethoxy-1-methylethyl)benzene (60.6 g).

The conversion of 4-(1-ethoxy-1-methylethyl)toluene is 98.5%; the yield of 1-ethoxymethyl-4-(1-ethoxy-1-methylethyl)benzene 12.5%, and the yield of 4-(1-ethoxy-1-methylethyl)benzaldehyde diethyl acetal is 26.0%; the selectivity for the latter is 30.2%.

EXAMPLE 5

Synthesis of 4-(1-methoxy-1-methylethyl)benzaldehyde from 4-(1-methoxy-1-methylethyl)benzaldehyde dimethyl acetal.

4-(1-Methoxy-1-methylethyl)benzaldehyde dimethyl acetal (1.8 kg) and water (1.8 kg) are heated in a stirred flask for about 1 h under reflux at 87° C. The mixture is cooled to about 25° C., and the two phases are separated. The organic phase is distilled with a head pressure of 4 mbar and head temperature of 105°–108° C. 4-(1-Methoxy-1-methylethyl)benzaldehyde (1314.6 g) is obtained. HNMR: $(CH_3)_2C$— 1.55 ppm (s), —$OCH_3$ 3.1 ppm (s), ArH 7.6 ppm (d), 7.90 ppm (d), —CHO 10.0 ppm (s). $n_D^{25} = 1.5264$. The yield is 97.3%.

EXAMPLE 6

In the manner described in Example 5, 4-(1-ethoxy-1-methylethyl)-benzaldehyde is obtained from 4-(1-ethoxy-1-methylethyl)benzaldehyde diethyl acetal. HNMR: 1.2 ppm (t), 1.6 ppm (s), 3.3 ppm (q), 7.65 ppm (d), 7.9 ppm (d), 10.5 ppm (s). Boiling range 269°–277° C., $n_D$ 1.5162.

We claim:

1. Benzaldehyde derivatives of the formula

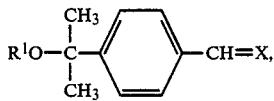

where X is an oxygen atom or two $R^2O$ groups and $R^1$ and $R^2$ are alkyl of 1–4 carbon atoms.

2. 4-(1-Alkoxy-1-methylethyl)benzaldehydes of formula

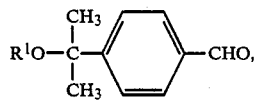

where $R^1$ is as given in claim 1.

3. 4-(1-Alkoxy-1-methylethyl)benzaldehyde dialkyl acetals of the formula III

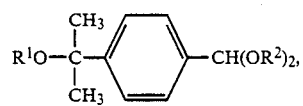

where $R^1$ and $R^2$ are as in claim 1.

4. 4-(1-Methoxy-1-methylethyl)benzaldehyde dimethyl acetal.

5. 4-(1-Methoxy-1-methylethyl)benzaldehyde.

6. 4-(1-Ethoxy-1-methylethyl)benzaldehyde diethyl acetal.

7. 4-(1-Ethoxy-1-methylethyl)benzaldehyde.

8. A process for the preparation of an acetal of the formula

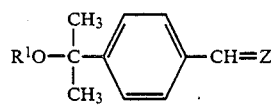

wherein X is an oxygen atom or two $R^2O$ groups and $R^1$ and $R^2$ are alkyl of 1 to 4 carbon atoms, which comprises:

electrochemically oxidizing a benzene derivative of the formula

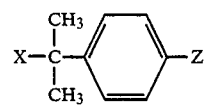

wherein X is hydrogen or the alkoxy group $R^1O$, Z is methyl, alkoxymethyl of the formula $R^2OCH_2$— or dialkyloxymethyl of the formula $(R^2O)_2CH$ with the proviso that X is hydrogen if Z is dialkyloxymethyl, said oxidation being carried out in the presence of an alkanol ROH, where R is alkyl of 1 to 4 carbon atoms, at a temperature of about 20° to 60° C. and in the presence of a conductive substance selected from the group consisting of neutral salts, acids and bases.

9. A process as claimed in claim 8 wherein the conductive substance is a neutral salt selected from the gorup consisting of fluorides, sulfonates, sulfates, tetrafluoroborates, phosphates and phosphonates.

10. A process as claimed in claim 8 wherein the conductive substance is an acid selected from the group consisting of sulfuric acid, alkyl sulfonic acids and aryl sulfonic acids.

11. A process as claimed in claim 8 wherein the conductive substance is a base selected from the group consisting of alkoxides and hydroxides.

* * * * *